(12) United States Patent
Geiger et al.

(10) Patent No.: US 7,889,897 B2
(45) Date of Patent: Feb. 15, 2011

(54) METHOD AND SYSTEM FOR DISPLAYING UNSEEN AREAS IN GUIDED TWO DIMENSIONAL COLON SCREENING

(75) Inventors: Bernhard Geiger, Cranbury, NJ (US); Sandra Sudarsky, Bedminster, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1272 days.

(21) Appl. No.: 11/438,617

(22) Filed: May 22, 2006

(65) Prior Publication Data

US 2007/0071297 A1    Mar. 29, 2007

Related U.S. Application Data

(60) Provisional application No. 60/684,639, filed on May 26, 2005.

(51) Int. Cl.
*G06K 9/00* (2006.01)
(52) U.S. Cl. .................................................. 382/128
(58) Field of Classification Search ......... 382/128–134; 128/920–930; 250/455–465; 356/39–49; 600/407–414, 424–426
See application file for complete search history.

(56) References Cited

U.S. PATENT DOCUMENTS

| | | | |
|---|---|---|---|
| 6,212,420 | B1 | 4/2001 | Wang et al. |
| 6,928,314 | B1 | 8/2005 | Johnson et al. |
| 2001/0031920 | A1 | 10/2001 | Kaufman et al. |
| 2005/0148848 | A1 | 7/2005 | Guang et al. |
| 2007/0003131 | A1 * | 1/2007 | Kaufman .................... 382/154 |

OTHER PUBLICATIONS

Ming Wan et al: "Automatic Centerline Extraction for Virtual Colonoscopy" IEEE Transactions on Medical Imaging, IEEE Service Center, Piscataway, NJ, US, vol. 21, No. 12, Dec. 2002, XPO 11076405 ISSN: 0278-0062 the whole document.

Kaufman A E et al: "Virtual colonoscopy" Communications of the ACM ACM USA, vol. 48, No. 2, Feb. 2005, pp. 37-41, XP002400961 ISSN: 0001-0782 cited in the application the whole document.

Macari M et al: "Comparison of time—efficient CT colonography with two—and three—dimensional colonic evaluation for detecting colorectal polyps." AJR. American Journal of Roentgenology. Jun. 2000, vol. 174, No. 6, Jun. 2000, pp. 1543-1549, XP002400962 ISSN: 0361-803X cited in the application the whole document.

(Continued)

*Primary Examiner*—Samir A Ahmed
*Assistant Examiner*—Atiba O Fitzpatrick
(74) *Attorney, Agent, or Firm*—Donald B. Paschburg (57) ABSTRACT

A method and system for displaying unseen areas in guided two dimensional (2D) colon screening, includes calculating segmentation and colon surface for a colon; calculating a centerline for the colon; designating as a current focus point a current point of intersection of a current portion of the centerline and a current cross-sectional image of a colon in a current image plane; and extracting a colon surface portion in a connected colon component containing the current focus point; and marking voxels of the colon surface portion as a "seen" area. Unseen areas of the colon surface are calculated by subtracting seen areas from the total colon area of observation. The unseen areas may then be displayed.

20 Claims, 6 Drawing Sheets

OTHER PUBLICATIONS

Hara A K et al: "Colorectal Polyp Detection With CT Colography: Two—Versus Three—Dimensional Techniques" Radiology, Oak Brook,IL, US, vol. 200, No. 1, 1996, pp. 49-54, XP008027074 ISSN: 0033-8419 cited in the application the whole document.

Sadleir R 3 T et al: "Fast Colon centreline Calculation using optimised 3D. topological thinning" Computerized Medical Imaging and Graphics, Pergamon Press; New York, NY, US, vol. 29, No. 4, Jun. 2005, pp. 251-258, XP004884889 ISSN: 0895-6111 the whole document.

* cited by examiner

METHOD AND SYSTEM FOR DISPLAYING UNSEEN AREAS IN GUIDED TWO DIMENSIONAL COLON SCREENING

CROSS-REFERENCE TO RELATED APPLICATIONS AND PRIORITY

Specific reference is hereby made to Provisional Application No. 60/684,639, entitled GUIDED TWO DIMENSIONAL COLON SCREENING, filed May 26, 2005 in the names of Bernhard Geiger and Sandra Sudarsky, the inventors in the present application, and of which the benefit of priority is claimed and whereof the disclosure is hereby incorporated herein by reference in its entirety.

Reference is also made to the patent application Ser. No. 11/438,499, entitled METHOD AND SYSTEM FOR GUIDED TWO DIMENSIONAL COLON SCREENING being filed on even date herewith in the names of Bernhard Geiger and Sandra Sudarsky, the inventors in the present application, and whereof the disclosure is hereby incorporated herein by reference in its entirety.

The present application relates generally to computer vision and imaging systems and, more particularly, to computerized imaging as applied to guided two dimensional colon screening.

BACKGROUND OF THE INVENTION

Virtual colonoscopy is a noninvasive technique for human colon cancer screening. Computed tomography (CT) or Magnetic resonance (MR) techniques are used to generate high-resolution cross-sectional images of the inner surface of the colon. The techniques are presently of importance in the field of medicine.

The technique of Virtual Colonoscopy is utilized to search the internal surface of the colon for polyps, using CT or MR data and computer graphics techniques, instead of performing an actual endoscopic examination with a real endoscope. This is desirable in order to reduce the necessity of performing an actual endoscopic examination and thereby reduce the need for patient preparation, patient discomfort, and any risk attendant upon such procedures. A "virtual endoscope" or camera is virtually directed through the colon, looking at the surface thereof to detect bumps that may indicate the presence of polyps. It is important to know whether the entire surface has been observed for examination, or whether there are patches or areas, typically concealed behind folds, that have not been seen or observed. Such patches could contain a polyp which would otherwise be missed in the virtual colonoscopy examination.

It has been described in the literature how such unseen patches can be detected in the case of a virtual three-dimensional (3D) flythrough; see, for example, A method for detecting unobserved regions in a virtual endoscopy system, Y. Hayashi, K. Mori, J. Toriwaki, Y. Suenaga, J. Hasegawa, Nagoya Univ. (J) CARS June 2001 (also SPIE may 2001)

Both CT and MR colonography generate a large number of images that must be interpreted by a radiologist for the presence of polyps; see Arie E. Kaufman, Sarang Lakare, Kevin Kreeger, Ingmar Bitter, Virtual Colonoscopy, Communications of the ACM, vol 48, No. 2, pp. 37-41, 2005.

Commonly used methods to examine these datasets include slice-by-slice viewing referred to as primary 2-dimensional (2D) reading and virtual flythroughs referred to as primary 3-dimensional (3D) reading. There appears to be little agreement in the literature as to which method results in the greatest rate of polyp detection; see Hara A K, Johnson C D, Reed J E, Ehman R L, Ilsrtup D M, Colorectal polyp detection with CT Colonography, two-versus three dimensional techniques, Radiology, 1996, 200:49-54.

A number of techniques have been proposed to facilitate 3D reading. Most of these techniques automate the navigation process by calculating the colonic centerline; see for example, U.S. patent application Ser. No. 10/842,972, filed May 11, 2004 in the name of Boissonnat, Jean-Daniel and Geiger, Bernhard and entitled METHOD AND APPARATUS FOR FAST AUTOMATIC CENTERLINE EXTRACTION FOR VIRTUAL ENDOSCOPY whereof the disclosure is incorporated herein by reference; Robert J. T. Sadleir, Paul F. Whelan, Colon Centerline Calculation for CT Colonography using Optimised 3D Topological Thinning, 1st International Symposium on 3D Data Processing Visualization and Transmission (3DPVT'02), pp. 800-804, 2002; I. Bitter, M. Sato, M. Bender, A. Kaufman, M. Wan, A Smooth, Accurate and Robust Centerline Extraction Algorithm, In Proc. of IEEE Visualisation, 2000; R. Chiou, A. Kaufman, Z. Liang, L. Hong, and M. Achniotou, Interactive Fly-Path Planning Using Potential Fields and Cell Decomposition for Virtual Endoscopy," IEEE Trans Nuclear Sciences, vol. 46, no. 4, pp. 1045-1049, 1999; and Samara Y, Fiebich M, Dachman A H, Kuniyoshi J K, Doi K, Hoffmann K R., Automated calculation of the centerline of the human colon on CT images, Acad Radiol. 1999 June; 6(6): 352-9. Other techniques automate the navigation process by computing the longest ray cast along the view direction. See, for example, U.S. patent application Ser. No. 10/322,326, filed Dec. 18, 2002 in the name of B. Geiger, and entitled AUTOMATIC NAVIGATION FOR VIRTUAL ENDOSCOPY; whereof the disclosure is incorporated herein by reference.

Another valuable help for 3D reading is the availability of techniques to get a map of colon wall patches that have not been observed during flythrough. Frequently, such areas are between deep Haustral folds. Such techniques have been proposed by, for example, F. M. Vos et. al. "A new visualization method for virtual colonoscopy", Lecture Notes in Computer Science, vol. 2208, 2001. However, these techniques are limited to 3D flythrough.

This is typically accomplished in three steps:
(a) The entire surface of the colon is calculated, by using colon segmentation techniques: (see, for example, the cited literature on colon segmentation below);
(b) during flythrough, all surface parts that have been rendered in the endoscopic view are marked as "seen"; and
(c) after flythrough has been completed, or at some other convenient time, the seen areas are subtracted from the complete surface, and the remaining "unseen" patches are calculated and displayed in a useful way.

Additional Information on centerline derivation techniques is provided in above-cited documents. See the above-cited publications by Robert, J. T. et al.; I. Bitter et al.; Samara, Y. et al.; Frimmel, H. et al.; and K. Mori et al.

Additional material on colon segmentation can be found in, for example, M. Sato, S. Lakare, M. Wan, A. Kaufman, Z. Liang, and M. Wax (2001) "An automatic colon segmentation for 3D virtual colonoscopy," IEICE Trans. Information and Systems, Vol. E84-D, No. 1, January 2001, pp. 201-208; and D. Chen, Z. Liang, M. Wax, Lihong Li, B. Li, and A. Kaufman (2000) "A Novel Approach to Extract Colon Lumen from CT Images for Virtual Colonoscopy," IEEE Transactions on Medical Imaging, Vol. 19, No. 12, December 2000, pp. 1220-1226.

Further basic information on segmentation, connected components, surface rendering and related topics can be found in a number of textbooks such as, for example, VIR- TUAL ENDOSCOPY AND RELATED 3D TECHNIQUES, edited by A. L. Baert; Springer, New York; 2001, 2002; FUNDAMENTALS OF IMAGE PROCESSING by Arthur R. Weeks, SPIE Optical Engineering Press & IEEE Press; 1996; IMAGE PROCESSING, ANALYSIS, AND MACHINE VISION, Second Edition, by Milan Sonka et al., PWS Publishing; 1999; and DIGITAL IMAGE PROCESSING, Second Edition, by Rafael C. Gonzalez et al., Prentice Hall; 2002.

However, the foregoing calculation in steps (a), (b), and (c) was heretofore only available for (3D) endoscopic flythrough and was limited thereto.

BRIEF SUMMARY OF THE INVENTION

It is herein recognized that very little has been proposed to facilitate slice-by-slice viewing. The convoluted structure typical of the colon makes slice-based visual inspection quite difficult. Generally, the radiologist must utilize manual control to browse through hundreds of two-dimensional images in search of polyps. Since the slice-based view does not provide a contiguous presentation of the inner surface of the colon, the radiologist must scroll up and down the axial images following a mental picture of the anatomical structure. An object of the present invention is to provide a method for reducing the difficulty of performing accurate slice-based visual inspection.

A basic technique for detecting colorectal polyps in CT data is to use axial images, by starting at the rectum, and carefully scrolling up and down through the images, following the colon. Since the colon is generally heavily convoluted, the scroll direction typically has to be repeatedly reversed. It is herein recognized that an important challenge for the radiologist is not to get distracted by the presence of other air filled structures in the images, such as the small intestine or other loops of the colon, which can cause pretermission or inadvertent skipping over of portions of the colon in the inspection process within which anomalies such as polyps may thus remain unobserved and undetected. It is therefore another object of the present invention to reduce any chance of inadvertent skipping over of portions of the colon in the inspection process within which anomalies such as polyps may thus remain unobserved and undetected.

By way of an example, a colon may exhibit portions looping up and down such that an image plane may intersect the colon in a plurality of places, which will appear as more or less circular cross-sections on the image plane. Beginning at an initial point, for example at the rectal end of the colon, the radiologist can follow a series of cross-sectional images of a first ascending segment of the colon which will appear on a succession of image planes at increasing distances from the initial point. Let the first ascending segment exhibit an inverted U arch, forming a ∩-shaped segment, and continue as a descending segment. The radiologist will then see two cross-sectional images on the image plane, corresponding to the ascending and descending segments, respectively. Also, other disjoint cross-sectional images corresponding to other loops of the colon may be present on the image plane so that a total of, for example, four cross-sectional images appear on the image plane.

As the image plane scrolls up, out of the four visible cross-sectional images, the radiologist will concentrate on the ascending segment as the currently observed portion. At some point, the image plane will reach above the arch, and the cross-sectional images of the ascending and descending segments will disappear. From a knowledge of anatomy, the radiologist will understand that this is attributable to the image plane being located above the arch and that somewhere is a continuation of the colon as the descending segment.

The image plane now scrolls down, and the radiologist must focus on the cross-sectional image of the descending segment, which is one of four cross-sectional images on the image plane. Should the radiologist through error or inadvertence at some point focus on another, incorrect cross-sectional image, a significant part might be missed, and/or valuable time lost in order to backtrack from the error. In the real world, there will typically be many more folds and the small intestine will be present in the region, which will increase the chances for error, especially for less experienced radiologists.

In accordance with another aspect of the invention, a method provides visual feedback to assist a radiologist during the 2-D reading process in guiding the navigation procedure and to assist in focusing attention while allowing for complete control by the radiologist by enabling unobserved areas to be calculated and displayed. It is herein recognized that this feature has hitherto been only available for 3D flythrough. In accordance with an aspect of the invention use is made of the centerline. In accordance with another aspect of the invention no pre-calculated centerline is required and a centerline is derived on the go. A centerline is defined as a sequence of 3D points contained inside the colon lumen that connect the two end points of the colon whereas each point is located as far as possible from the colon wall.

It is known that an approximate centerline through the colon can be provided. See, for example, the above-cited publications by Robert, J. T. et al.; I. Bitter et al.; Samara, Y. et al.; Frimmel, H. et al.; and K. Mori et al.

In accordance with another aspect of the invention, a method for displaying unseen areas in guided two dimensional (2D) colon screening, comprising: calculating segmentation and colon surface for a colon; calculating a centerline for the colon; designating as a first current focus point a current point of intersection of a first current portion of the centerline and a first current cross-sectional image of a colon in a first current image plane; and extracting a first colon surface portion in a first connected colon component containing the first current focus point marking voxels of the first colon surface portion as a first "seen" area.

In accordance with another aspect of the invention, the step of calculating segmentation and colon surface for a colon includes a step of calculating a total colon surface area.

In accordance with another aspect, the invention includes a step of calculating unseen areas of the colon surface by subtracting seen areas from the total colon area.

In accordance with another aspect of the invention, the step of calculating a total colon area is defined as calculating a 3D representation of the total colon area and the step of subtracting seen areas from the total colon area is defined as a set subtraction on a set of surface voxels.

In accordance with another aspect of the invention, a step is included for scrolling to a second cross-sectional image of a colon in a second image plane; designating as a second current focus point a second current point of intersection of the centerline and a second current cross-sectional image of a colon in a second current image plane; and extracting a first colon surface portion in a second connected colon component containing the second current focus point marking voxels of the second colon surface portion as a second "seen" area.

In accordance with another aspect of the invention, the step of calculating segmentation and colon surface for a colon includes a step of calculating a total colon surface area.

In accordance with another aspect of the invention, the invention includes a step of calculating unseen areas of the colon surface by subtracting the first and second seen areas from a total colon area.

In accordance with another aspect of the invention, the step of calculating a total colon area is defined as calculating a 3D representation of the total colon area and the step of subtracting seen areas from the total colon area is defined as a set subtraction on a set of surface voxels.

In accordance with another aspect of the invention, the invention includes a step of displaying the unseen areas.

In accordance with another aspect of the invention, a method for displaying unseen areas in guided two dimensional (2D) colon screening, comprises: calculating segmentation and colon surface for a colon; calculating a centerline for the colon; marking, in a current cross-sectional image of a colon in a current image plane, a current point of intersection of the centerline and the current image plane as a focus point; displaying the current cross-sectional; extracting a colon surface portion in a connected colon component containing the focus point; and marking voxels of the colon surface portion as "seen".

In accordance with another aspect of the invention, a method includes a step of calculating unseen areas of the colon surface by subtracting seen areas from a predetermined total colon surface area.

In accordance with another aspect of the invention, a method includes a step of displaying the unseen areas.

In accordance with another aspect of the invention, the step of marking the voxels of the colon surface portion as "seen" comprises coloring in a distinctive color.

In accordance with another aspect of the invention, a method comprises: fading the first distinctive color in accordance with the distance of the respective portions of the centerline from the current image, the distance being in terms of sequence progression along the centerline.

In accordance with another aspect of the invention, in the event of a plurality of points of intersection being present, marking only that portion of the centerline corresponding to a point of intersection of the plurality which is closest to the current cross-sectional image, in terms of sequence progression along the centerline.

In accordance with another aspect of the invention, a method includes a step of calculating unseen areas of the colon surface by subtracting seen areas from a predetermined total colon surface area.

In accordance with another aspect of the invention, method includes a step of displaying the unseen areas.

In accordance with another aspect of the invention, the step of marking the voxels of the colon surface portion as "seen" comprises coloring in a distinctive color.

In accordance with another aspect of the invention, a method comprises: fading the distinctive color in accordance with the distance of the respective portions of the centerline from the current image, the distance being in terms of sequence progression along the centerline.

In accordance with another aspect of the invention, a method for displaying unseen areas in guided two dimensional (2D) colon screening, comprises: calculating segmentation and colon surface for a colon; utilizing a two dimensional (2D) image reading process of observing an axial cross-sectional image of a colon on an axial image plane; scrolling through a series of image plane positions by scrolling from a first axial image plane position looking into the colon; deriving a centerline for the series of image plane positions; and calculating, for each image plane position a respective point of intersection of the centerline of the colon therewith; at a each currently observed image plane position, marking a current portion of the centerline at its respective point of intersection as a focus point and in the event of a plurality of points of intersection of an image plane with the centerline being present, marking as the focus point only that portion of the centerline corresponding to a point of intersection of the plurality which is closest to the current portion of the centerline; extracting a colon surface portion in a connected colon component containing the focus point; marking voxels of the colon surface portion as "seen"; calculating unseen areas of the colon surface by subtracting seen areas from a predetermined total colon surface area; scrolling to a next image as the next currently observed image plane position; removing the marking as a focus point; and marking a next respective current portion of the centerline associated with its respective point of intersection with the next currently observed image plane position as a next focus point.

In accordance with another aspect of the invention, the step of marking the voxels of the colon surface portion as "seen" comprises coloring in a first distinctive color.

In accordance with another aspect of the invention, a method comprises: fading the first distinctive color in accordance with the distance of the respective portions of the centerline from the current image, the distance being in terms of sequence progression along the centerline.

In accordance with another aspect of the invention, the step of marking the voxels of the colon surface portion as "seen" comprises marking the voxels in a first distinctive manner.

In accordance with another aspect of the invention, a method comprises: fading the first distinctive first distinctive marking manner to an increasing degree in accordance with the distance of the respective portions of the centerline from the current image, the distance being in terms of sequence progression along the centerline.

In accordance with another aspect of the invention, a system for displaying unseen areas in guided two dimensional (2D) colon screening, comprises: a memory device for storing a program and other data; and a processor in communication with the memory device, the processor being operative with the program to perform: calculating segmentation and colon surface for a colon; calculating a centerline for the colon; designating as a first current focus point a current point of intersection of a first current portion of the centerline and a first current cross-sectional image of a colon in a first current image plane; and extracting a first colon surface portion in a first connected colon component containing the first current focus point marking voxels of the first colon surface portion as a first "seen" area.

In accordance with another aspect of the invention, a system for displaying unseen areas in guided two dimensional (2D) colon screening, comprises: memory apparatus for storing a program and other data; and processor apparatus in communication with the memory device, the processor apparatus being operative with the program to perform: calculating segmentation and colon surface for a colon; calculating a centerline for the colon; designating as a first current focus point a current point of intersection of a first current portion of the centerline and a first current cross-sectional image of a colon in a first current image plane; and extracting a first colon surface portion in a first connected colon component containing the first current focus point marking voxels of the first colon surface portion as a first "seen" area.

In accordance with another aspect of the invention, a computer program product comprises a computer useable medium having computer program logic recorded thereon for program code for displaying unseen areas in guided two dimensional (2D) colon screening, for programming a computer for: calculating segmentation and colon surface for a colon; calculating a centerline for the colon; utilizing a two dimensional (2D) image reading process of observing an axial cross-sectional image of a colon on an axial image plane; scrolling through a series of image plane positions; marking, in a current cross-sectional image of a colon in a current image plane, a current point of intersection of a current portion of a centerline of the current cross-sectional image and the current image plane; and extracting a colon surface portion in a connected colon component containing the focus point; and marking voxels of the colon surface portion as "seen".

In accordance with another aspect of the invention, a method and system for displaying unseen areas in guided two dimensional (2D) colon screening, includes calculating segmentation and colon surface for a colon; calculating a centerline for the colon; designating as a current focus point a current point of intersection of a current portion of the centerline and a current cross-sectional image of a colon in a current image plane; and extracting a colon surface portion in a connected colon component containing the current focus point; and marking voxels of the colon surface portion as a "seen" area. Unseen areas of the colon surface are calculated by subtracting seen areas from the total colon area of observation. The unseen areas are then displayed.

BRIEF DESCRIPTION OF THE SEVERAL VIEWS OF THE DRAWINGS

The invention will be more fully understood from the following detailed description, in conjunction with the drawing, not necessarily to scale, in which.

DETAILED DESCRIPTION OF THE INVENTION

In the following description, functions and systems well known in the art are not set forth in detail so as to avoid obscuring the description of the invention with unnecessary details. Provisional application No. 60/684,639 entitled GUIDED TWO DIMENSIONAL COLON SCREENING and the non-provisional patent application entitled METHOD AND SYSTEM FOR GUIDED TWO DIMENSIONAL COLON SCREENING, being filed on even date herewith, disclose and teach a method and system for guided two dimensional colon screening. Reference is made to this non-provisional patent application for a more detailed description of the method and system disclosed therein.

Briefly, the afore-mentioned patent applications for guiding image reading for colon screening disclose a method and system for colon screening includes scrolling through a succession of two dimensional (2D) cross-sectional images of a colon in respective image planes. A point of intersection with a current image plane with the centerline of the colon is marked in a first color in the current cross-sectional image. As the scrolling proceeds and a new current cross-sectional image in a respective image plane is visited, a new point of intersection is marked in the current cross-sectional image in the first color and the prior point of intersection is projected onto the new current cross-sectional image and marked in a second color.

It will be understood and borne in mind that, in accordance with typical present-day computer imaging procedures, the centerline will generally be represented by a closely-spaced series of points or dots as stated above, and these points are spaced in accordance with some convenient desired level of resolution.

In reference to the method and system for colon screening referred to above, in the current image, a portion of the centerline is marked, for example in red, at the point of intersection of the center line with the current image plane. The marking serves to provide a "focus point" and will continue to indicate the status of the current image as such until a further image becomes the current image, the former current image passing into a category of prior images, whereupon the red marking will be replaced or overwritten by, for example, a green marking indicating that the image is marked as having been visited.

In the event of a plurality of points of intersection of the current image with the centerline being present, marking in the second color, only that point of intersection out of the plurality exhibiting the least separation distance from the current point of intersection, the separation distance being measured in terms of sequence progression along the centerline.

Furthermore, in reference to the method and system for colon screening referred to above, in the event the next image plane position intersects the centerline at a plurality of points of intersection, then selecting out of the plurality as the second point of intersection that which is closest to the first point of intersection, measured in terms of sequence progression along the centerline. Thereafter, performing scrolling to yet further cross-sectional images on yet further image planes and repeating the foregoing steps, mutatis mutandis; then projecting foregoing points of intersection on each successive current image plane; and if the separation distance between a projected point and the current point of intersection is within a given criterion, that projected point is displayed and otherwise not. The given criterion may be defined by one of: (a) user action, and (b) derivation from the distance between successive image planes. The separation distance can be in terms of sequence progression along said centerline and/or the Euclidean distance.

Thus, in summary and by way of example, in reference to the method and system for colon screening referred to above, the point of intersection is marked in a first color in the current image, for example red, and the previous, or preceding, points of intersection along the order of the centerline are drawn in a second color, for example, green as they appear projected into the current image plane. The second color indicates "visited" portions of the centerline and is faded in accordance with the distance from the current image plane, in terms of the sequence progression along the centerline to the current image plane. Thus, previous points of intersection appear as corresponding points projected onto the current image plane. This technique provides guidance during the navigation. The red point provides the focus of attention, or focus point referred to above, as one browses through the slices following the anatomical structure of the colon. If the red point is not visible, then it is also an indication that scrolling has been done in the wrong direction. The green portion provides an indication of previous path direction, with green points added most recently being the brightest and earlier added green points fading to less bright levels. The degree of fading relates to the separation distance from a current cross-sectional image plane where the distance can be in terms of sequence progression along said centerline and/or the Euclidean distance.

In reference now to the present invention, the non-visited areas of the colon under observation in the 2D virtual procedure are calculated in accordance with the present invention for workflows based on a 2D reading.

The colon wall is calculated. By considering the 2D colon section that contains the "focus point" as referred to above, for example, a red dot to mark it as "visited", the voxels of the portion of the colon wall that contains the focus point are set in a mask to the status of "seen", as in step (b) of the prior art 3 steps set forth above for the calculation of the unseen patches during flythrough.

FIG. 3A-3D shows typical operation of preliminary steps of the present invention by way of an exemplary embodiment in relation to axial images of a colon. The visible portion of the centerline superimposed onto the axial images is shown at different cross-sections. The red points, serving as current focus points, correspond to the newly added element to the "visited" part of the centerline and the green to previously visited portions.

Figure 4:
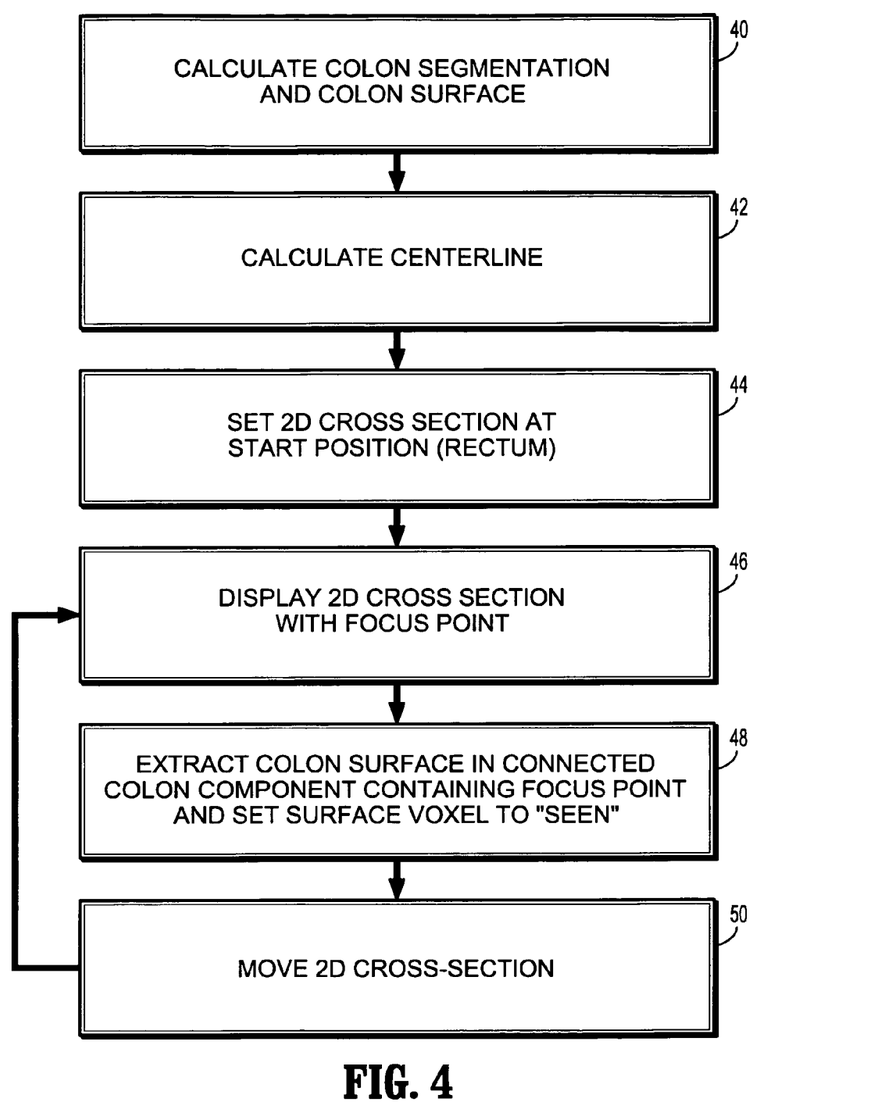
FIGS. 4 and 5 show flow chart diagrams helpful to gaining a fuller understanding of the invention.

Referring next to the flow diagram shown in FIG. 4, the colon segmentation and colon surface are calculated in step 40. The centerline is calculated in step 42; the centerline may be available from a previous calculation or it may be performed on the fly. See the foregoing materials on centerline calculation. In step 44, the 2D cross section is set at the start position, typically at the rectum. At step 46, the 2D cross section is displayed with current focus point and is so marked as a focus point.

The calculation and marking of the focus point have been explained above. For additional information, reference is made to the aforementioned patent applications incorporated herein by reference, namely, provisional application No. 60/684,639 entitled GUIDED TWO DIMENSIONAL COLON SCREENING and non-provisional patent application entitled METHOD AND SYSTEM FOR GUIDED TWO DIMENSIONAL COLON SCREENING.

At step 48, the colon surface in the 2D cross-section is extracted in the connected colon component containing the current focus point and the surface voxel in the 3D segmentation are set to the status of "seen". This can be done, for example, by starting a 2D region growing from the focus point, including all voxels within a Hounsfield range that includes colon lumen values (air). Voxels with a neighbor having a non-lumen value are considered colon surface voxels.

In step 50, the 2D cross-section is moved. Steps 46, 48, and 50 are now performed with the moved 2D cross section with its current focus point.

Figure 5:
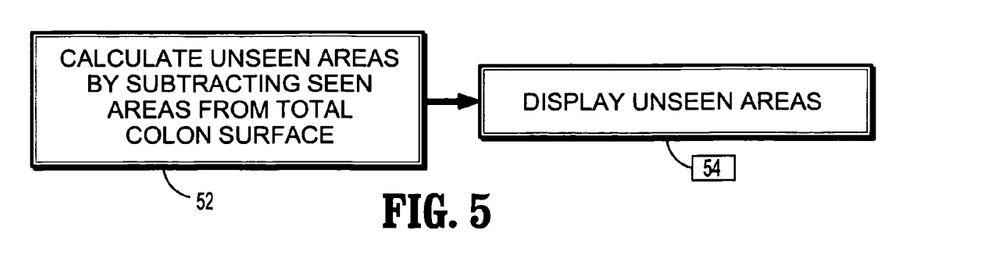

Referring next to the flow diagram shown in FIG. 5, the unseen areas in the 3D segmentation are then calculated in step 52 by subtracting the seen areas determined in step 48 from the total colon surface. The calculated unseen areas are then displayed, step 54.

It will be understood that in the sense typically pertaining to the field of the present invention and as used herein, calculating an area does not mean calculating an area in the sense of calculating square inches or square millimeters but rather, it means calculating a 3D representation of the area or a map. Likewise, subtracting the seen areas from the total colon surface does not mean simply subtracting numbers, for example, of square millimeters; rather it is a set subtraction on the set of surface voxels.

Figure 1:
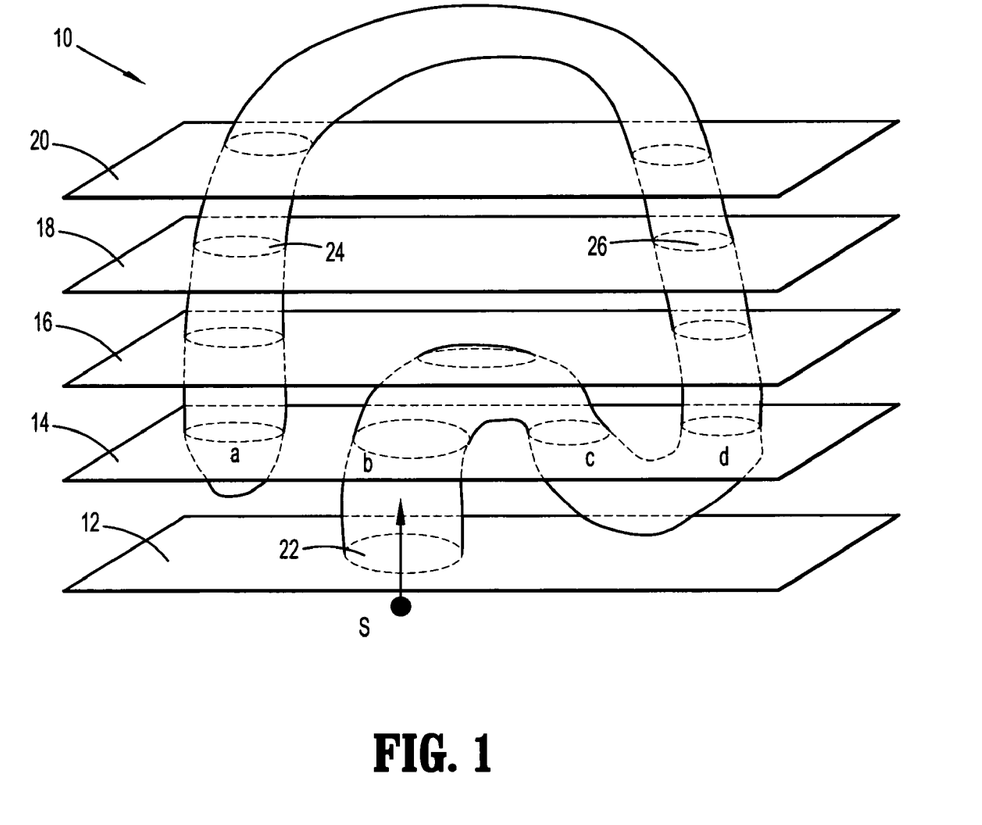
FIG. 1 shows an example of a simplified diagrammatic image of a colon, together with axial cross sections positions, helpful to gaining a fuller understanding of the present invention.
Figure 2:
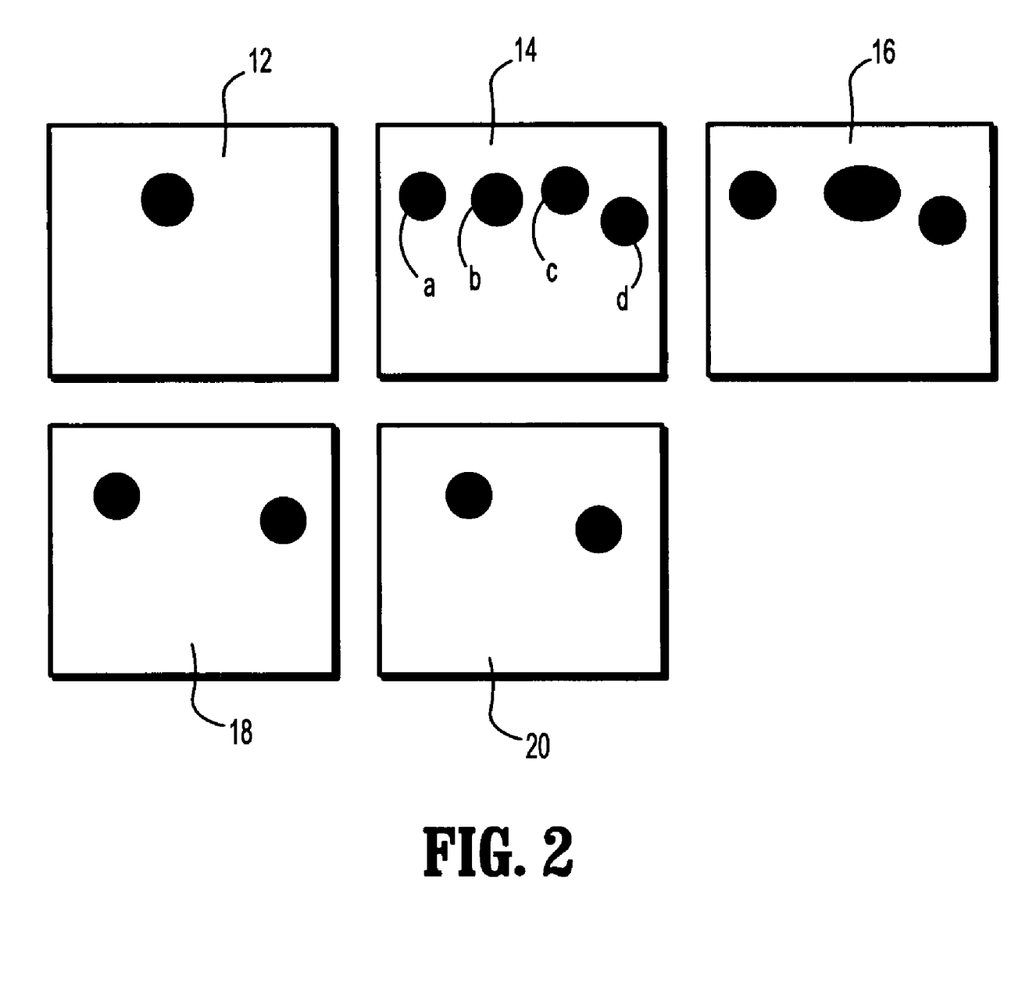
FIG. 2 shows in a simplified diagrammatic form axial images corresponding to the constellation in FIG. 1.
Figure 3:
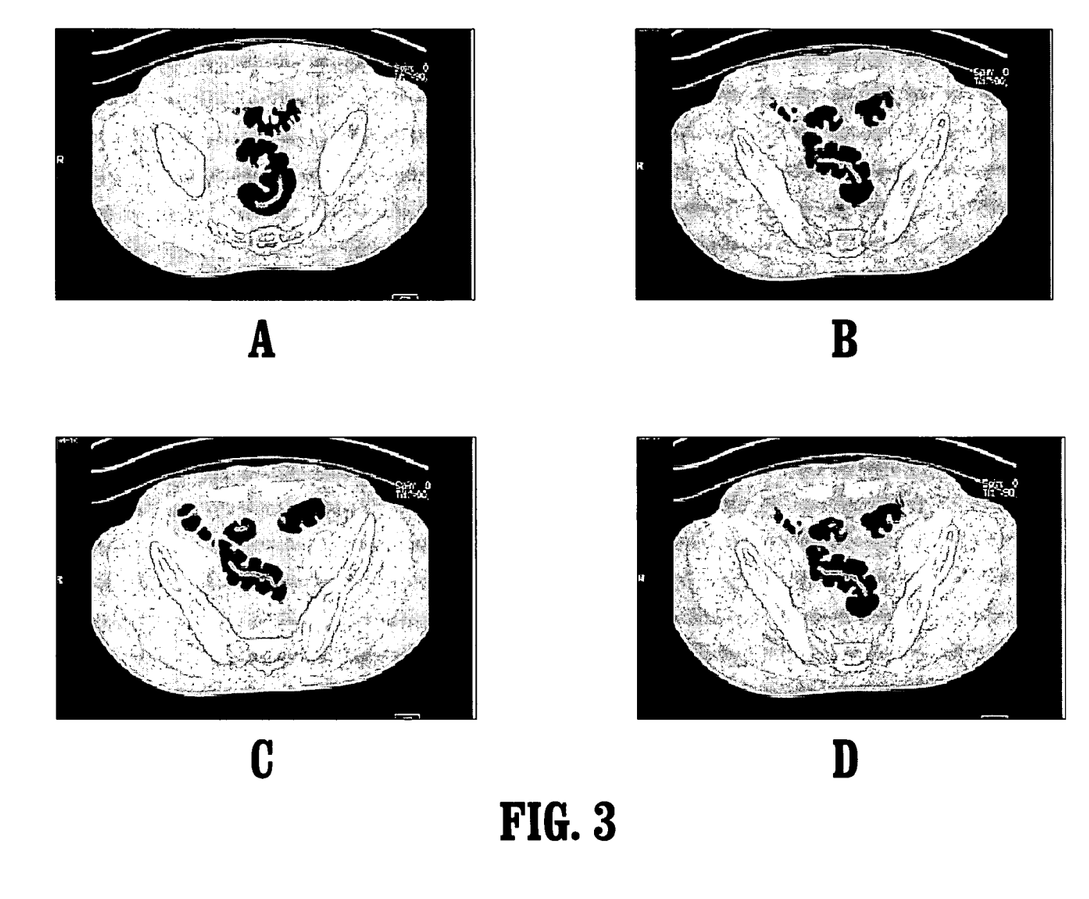
FIG. 3 shows typical operation of preliminary steps in an exemplary embodiment in accordance with the present invention in relation to axial images of a colon.
Figure 6:
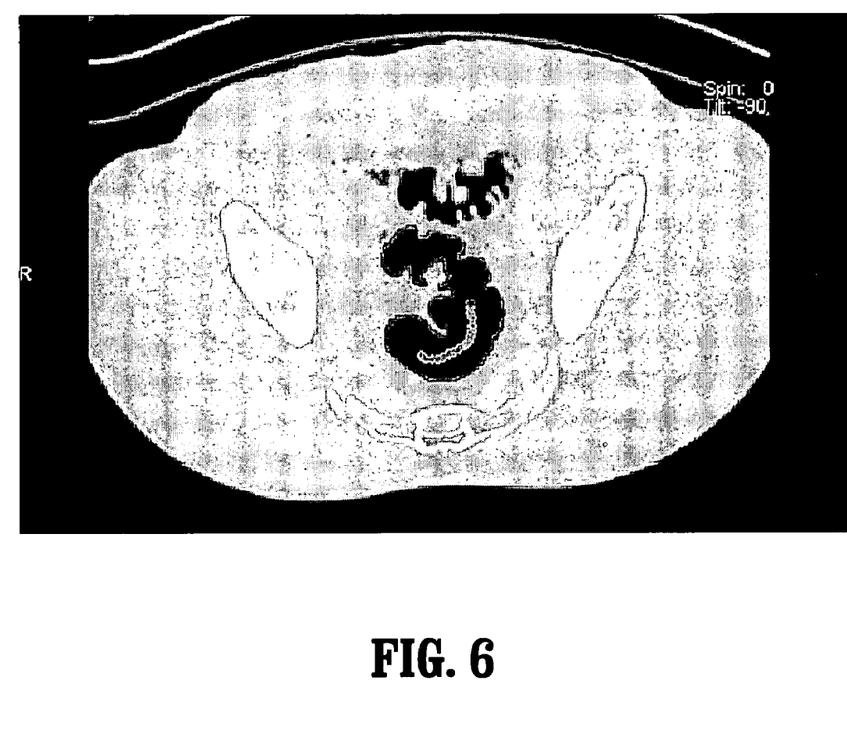
FIG. 6 shows typical operation in accordance with principles of the present invention.

FIG. 6 shows a display of the newly seen or observed surface voxels corresponding to FIG. 3A. Unseen areas can be displayed in a 3D colon rendering, or in a 3D endoscopic rendering, or on 2D images, using color to indicate unseen areas. In FIG. 6, the green line shows the visited portion of the centerline in the 2D procedure and the red line indicates marked voxels of a colon surface portion as a "seen" area.

The steps 52 and 54 shown in the flow diagram in FIG. 5 may be performed following the performance of step 48 with each 2D cross-section. However steps 52 and 54 need not be performed concurrently with or immediately following the preceding steps but may also be performed at some other convenient time during the procedure. For example, these steps can be executed on demand, for example after the user has finished looking at the colon, or at regular intervals, or other intervals, to continuously update the unseen area display. Furthermore, seen areas relating to a number of 2D cross-sections may be totalized in a subtotal and the subtotal may then be subtracted from the total colon surface to obtain the unseen area. Having the total number of voxels in the colon surface and the seen voxels, the percentage of the surface that remain unseen can then be computed.

It is noted that the computation of the unseen areas is independent of the unseen area display. Every surface voxel is initially marked as unseen. During step 48 some voxels are internally marked as seen. Based on the seen/unseen information, the unseen areas can be displayed on demand.

As will be understood from the foregoing, the method in accordance with the present invention supports 2D reading of colonoscopy data, by calculating and displaying unseen areas. Concomitant benefits and advantages include a reduced risk of missing parts, faster examination by avoiding wrong decisions, and the automatic verification of unobserved surfaces.

As has been mentioned above, the computation of unseen areas during primary 3D readings has been previously proposed. However, it is noted that calculation of unseen areas for 2D browsing is a different matter from the calculation of unseen areas with flythrough. Some radiologists appear to prefer to analyze CT data sets using a primary 2D approach while others prefer a 3D approach and yet others combine both. There does not appear to be any clear consensus in the literature as to which technique is better. The present invention discloses a method and system for computing unseen areas to be used during primary 2D readings.

It is also noted that segmentation and centerline calculation can be done without performing a prior flythrough and may be performed with comparatively fast techniques. In known prior art systems, however, unseen areas were only available by doing a complete flythrough. A number of physicians appear to prefer performing a complete "scroll-through" in 2D, and then only look at a discrete number of 3D locations when they find something needing further investigation. In such cases, the present invention is particularly useful.

Thus, the present invention also provides a technique for radiologists who prefer to use 2D readings with a technique for verifying that they did not miss a part of the colon.

The method in accordance with the invention can also find an important application as a guided learning tool particularly for less inexperienced radiologists to gain additional skills.

It will be understood that the invention is useful to virtual colonoscopy as well as to various other virtual endoscopic type examinations.

Figure 7:
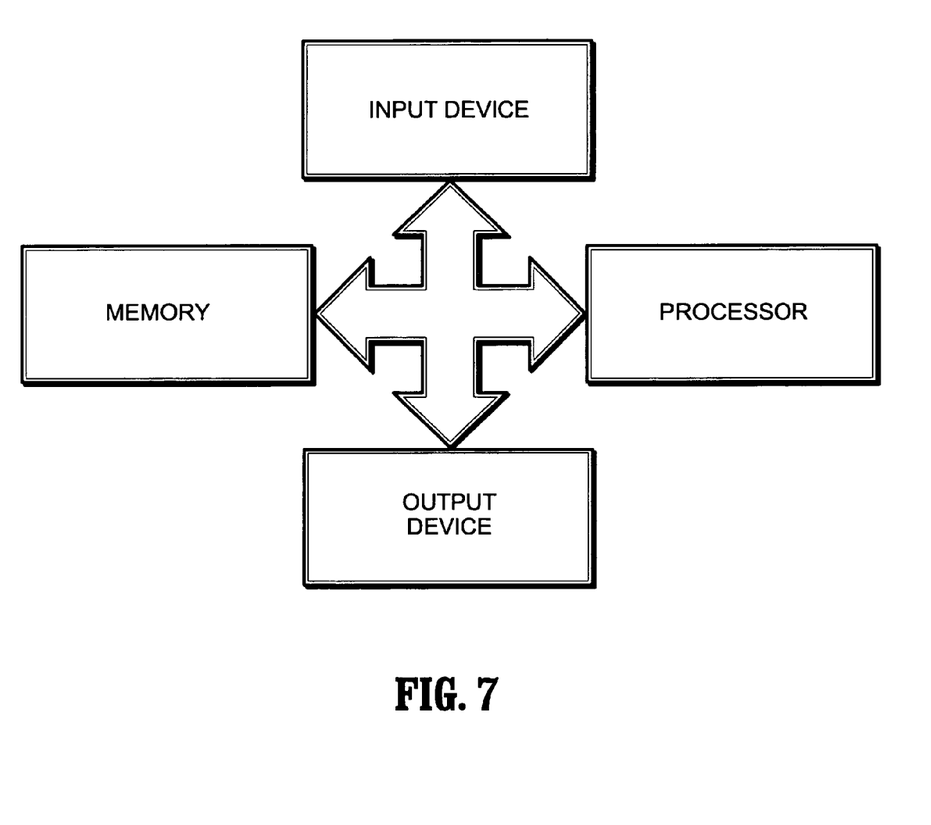
FIG. 7 shows in schematic form the application of a programmable digital computer for implementation of the invention.

As will be apparent, the present invention is best intended to be implemented with the use and application of imaging equipment in conjunction with a programmed digital computer. FIG. 7 shows in basic schematic form a digital processor coupled for two way data communication with an input device, an output device, and a memory device for storing a program and other data. The input device is so designated in broad terms as a device for providing an appropriate image or images for processing in accordance with the present invention. For example, the input may be from an imaging device, such as a device incorporated in a CATSCAN, X-ray machine, an MRI or other device, or a stored image, or by communication with another computer or device by way of direct connection, a modulated infrared beam, radio, land line, facsimile, or satellite as, for example, by way of the World Wide Web or Internet, or any other appropriate source of such data. The output device may include a computer type display device using any suitable apparatus such as a cathode-ray kinescope tube, a plasma display, liquid crystal display, and so forth, or it may or may not include a device for rendering an image and may include a memory device or part of the memory device of FIG. 7 for storing an image for further processing, or for viewing, or evaluation, as may be convenient, or it may utilize a connection or coupling including such as are noted above in relation to the input device. The processor is operative with a program set up in accordance with the present invention for implementing steps of the invention. Such a programmed computer may interface readily through communications media such as land line, radio, the Internet, and so forth for image data acquisition and transmission.

The invention may be readily implemented, at least in part, in a software memory device and packaged in that form as a software product. This can be in the form of a computer program product comprising a computer useable medium having computer program logic recorded thereon for program code for performing the method of the present invention.

The present invention has also been explained in part by way of examples using illustrative exemplary embodiments. It will be understood that the description by way of exemplary embodiments is not intended to be limiting and that, while the present invention is broadly applicable, it is helpful to also illustrate its principles, without loss of generality, by way of exemplary embodiments relating to an important field of application for the present invention, namely, to computer vision and imaging systems and, more particularly, to computerized imaging as applied to guided two dimensional colon screening.

It will also be understood that various changes and substitutions not necessarily herein explicitly described may be made without departing from the spirit and scope of the invention which is defined by the claims following.

What is claimed is:

1. A method for displaying unseen areas in guided two dimensional (2D) colon screening, comprising:
   calculating segmentation and colon surface for a colon;
   calculating a centerline for said colon;
   utilizing a 2D image reading process of observing an axial cross-sectional image of said colon on an axial image plane for:
   marking in a current cross-sectional image of a colon in a current image plane, a current point of intersection of said centerline and said current image plane as a focus point;
   displaying said current cross-sectional image;
   extracting a colon surface portion in a connected colon component containing said focus point;
   marking voxels of said colon surface portion as "seen", wherein said step of marking said voxels of said colon surface portion as "seen" comprises coloring in a distinctive color; and
   fading said distinctive color in accordance with the distance of said respective portions of said centerline from said current image, said distance being in terms of sequence progression along said centerline.

2. A method as recited in claim 1 comprising:
   in the event of a plurality of points of intersection being present, marking only that portion of said centerline corresponding to a point of intersection of said plurality which is closest to said current cross-sectional image, in terms of sequence progression along said centerline.

3. A method as recited in claim 2, including a step of calculating unseen areas of said colon surface by subtracting seen areas from a predetermined total colon surface area.

4. A method as recited in claim 3, including a step of displaying said unseen areas.

5. A method for displaying unseen areas in guided two dimensional (2D) colon screening, comprising:
   calculating segmentation and colon surface for a colon;
   calculating a centerline for said colon;
   utilizing a two dimensional (2D) image reading process of observing an axial cross-sectional image of a colon on an axial image plane for:
   scrolling through a series of 2D image plane positions;
   marking, in a current cross-sectional 2D image of a colon in a current image plane, a current point of intersection of a current portion of a centerline of said current cross-sectional 2D image and said current image plane as a focus point;
   extracting a colon surface portion in a connected colon component containing said focus point;
   marking voxels of said colon surface portion as "seen", wherein said step of marking said voxels of said colon surface portion as "seen" comprises coloring in a distinctive color; and
   fading said distinctive color in accordance with the distance of said respective portions of said centerline from said current image, said distance being in terms of sequence progression along said centerline.

6. A method as recited in claim 5 comprising:
   in the event of a plurality of points of intersection being present, marking only that portion of said centerline corresponding to a point of intersection of said plurality which is closest to said current cross-sectional image in terms of sequence progression along said centerline.

7. A method as recited in claim 6, including a step of calculating unseen areas of said colon surface by subtracting seen areas from a predetermined total colon surface area.

8. A method as recited in claim 7, wherein said step of calculating a total colon area is defined as calculating a 3D representation of said total colon area and said step of subtracting seen areas from said total colon area is defined as a set subtraction on a set of surface voxels.

9. A method as recited in claim 7, including a step of displaying said unseen areas.

10. A method as recited in claim 6, wherein said step of marking said voxels of said colon surface portion as "seen" comprises coloring in a distinctive color.

11. A method as recited in claim 10, comprising:
    fading said distinctive color in accordance with the distance of said respective portions of said centerline from said current image.

12. A method for displaying unseen areas in guided two dimensional (2D) colon screening, comprising:

calculating segmentation and colon surface for a colon;

utilizing a two dimensional (2D) image reading process of observing an axial cross-sectional image of a colon on an axial image plane;

scrolling through a series of image plane positions by scrolling from an axial image plane position looking into said colon;

deriving a centerline for said series of image plane positions; and calculating, for each image plane position a respective point of intersection of said centerline of said colon therewith;

at each currently observed image plane position, marking a current portion of said centerline at its respective point of intersection as a focus point and in the event of a plurality of points of intersection of an image plane with said centerline being present, marking as said focus point only that portion of said centerline corresponding to a point of intersection of said plurality which is closest to said current portion of said centerline;

extracting a colon surface portion in a connected colon component containing said focus point;

marking voxels of said colon surface portion as "seen";

calculating unseen areas of said colon surface by subtracting seen areas from a predetermined total colon surface area;

scrolling to a next image as the next currently observed image plane position;

removing said marking as a focus point; and marking a next respective current portion of said centerline associated with its respective point of intersection with said next currently observed image plane position as a next focus point.

13. A method as recited in claim 12, wherein said step of marking said voxels of said colon surface portion as "seen" comprises coloring in a distinctive color.

14. A method as recited in claim 13, comprising:

fading said distinctive color in accordance with the distance of said respective portions of said centerline from said current image, said distance being in terms of at least one of sequence progression along said centerline and Euclidean distance.

15. A method as recited in claim 12, wherein said step of marking said voxels of said colon surface portion as "seen" comprises marking said voxels in a distinctive manner.

16. A method as recited in claim 15, comprising:

fading said distinctive marking manner to an increasing degree in accordance with the distance of said respective portions of said centerline from said current image, said distance being in terms of at least one of sequence progression along said centerline and Euclidean distance.

17. A method for displaying unseen areas in guided two dimensional (2D) colon screening, comprising:

calculating segmentation and colon surface for a colon;

utilizing a two dimensional (2D) image reading process of observing an axial cross-sectional image of a colon on an axial image plane;

scrolling through a series of image plane positions by scrolling from an axial image plane position looking into said colon;

deriving a centerline for said series of image plane positions;

calculating, for each image plane position a respective point of intersection of said centerline of said colon therewith;

at each currently observed image plane position, marking a current portion of said centerline at its respective point of intersection in a first distinctive manner as a focus point;

in the event of a plurality of points of intersection of an image plane with said centerline being present, marking in said first distinctive manner only that portion of said centerline corresponding to a point of intersection of said plurality which is closest to said current portion of said centerline;

extracting a colon surface portion in a connected colon component containing said focus point marking voxels of said colon surface portion as first "seen" areas;

calculating first unseen areas of said colon surface by subtracting seen areas from a predetermined total colon surface area;

scrolling to a next image as the next currently observed image plane position;

overwriting said first distinctive manner with a second distinctive manner;

marking a next respective current portion of said centerline associated with its respective point of intersection with said next currently observed image plane position in said first distinctive manner as a next focus point;

extracting a next colon surface portion in a connected colon component containing said focus point marking voxels of said colon surface portion as second "seen" areas; and calculating next unseen areas of said colon surface by subtracting said second seen areas from a said first seen areas.

18. A method as recited in claim 17, wherein said step of calculating a total colon area is defined as calculating a 3D representation of said total colon area and said step of subtracting seen areas from said total colon area is defined as a set subtraction on a set of surface voxels.

19. A method as recited in claim 17, comprising:

scrolling to yet further cross-sectional images on yet further image planes and repeating the foregoing steps, mutatis mutandis;

projecting on each image plane each respective point of intersection of the foregoing centerline; and if the distance between a projected point of intersection and the current point of intersection is within a given criterion, that projected point is designated as a current focus point.

20. A method as recited in claim 19, comprising:

determining said given criterion by one of:

(a) user action, and (b) derivation from the distance between successive image planes.

* * * * *